United States Patent [19]

Assmus et al.

[11] Patent Number: 5,708,021
[45] Date of Patent: Jan. 13, 1998

[54] DEBITTERED RANITIDINE PREPARATION

[75] Inventors: Manfred Assmus, Bickenbach; Hans-Ulrich Petereit, Darmstadt, both of Germany

[73] Assignee: Roehm GmbH Chemische Fabrik, Darmstadt, Germany

[21] Appl. No.: 574,340

[22] Filed: Dec. 18, 1995

[30] Foreign Application Priority Data

Dec. 17, 1994 [DE] Germany ............... 9420259 U

[51] Int. Cl.$^6$ .................................. A61K 31/34
[52] U.S. Cl. .................................... 514/471
[58] Field of Search ................. 514/471, 772.3

[56] References Cited

U.S. PATENT DOCUMENTS

| | | |
|---|---|---|
| 3,629,392 | 12/1971 | Banker et al. . |
| 4,539,199 | 9/1985 | Orban et al. . |
| 5,219,563 | 6/1993 | Douglas et al. ............... 424/78.1 |
| 5,399,556 | 3/1995 | Clitherow et al. ............ 514/184 |

FOREIGN PATENT DOCUMENTS 664 284   2/1988   Switzerland .

OTHER PUBLICATIONS

Derwent Abstracts, AN 91–081795, EP–A–417 488, Mar. 20, 1990.
Derwent Abstracts, AN 79–42556B, DE–A–27 52 705, May 31, 1979.
Derwent Abstract No. 91–081871 of EP 417588, 1991.
Remington's Pharmaceutical Sciences, 16th ed. pp. 202–203, (1980).

*Primary Examiner*—Raymond Henley, III
*Attorney, Agent, or Firm*—Oblon, Spivak, McClelland, Maier & Neustadt, P.C.

[57] ABSTRACT

Ranitidine salts with polycarboxylic acids, such as copolymers of acrylic and/or methacrylic acid with their lower alkyl esters, are water-soluble salts with a very reduced bitter taste. The salts are suitable as liquid gastritis preparations.

14 Claims, No Drawings

DEBITTERED RANITIDINE PREPARATION

BACKGROUND OF THE INVENTION

1. Field of the Invention

The invention concerns a ranitidine preparation, completely free or substantially free of bitter taste, in particular in the form of an aqueous solution. Ranitidine is the generic name of N-[2-(dimethylaminomethylfurfurylthio)ethyl)N'-methyl-2-nitro-1,1-ethylenediamine shown below, which is used for the treatment of gastritis.

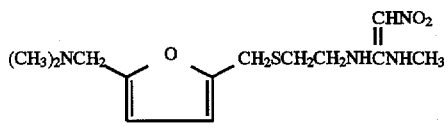

The preferred form of use is ranitidine hydrochloride, which as an aqueous solution, tastes extremely bitter, and, therefore, is hardly used in this form. The hydrochloride is predominantly taken in encased or microencapsulated form, for example, in the form of film tablets or coated pellets.

2. Discussion of the Background

A method is known for the preparation of compositions with neutral taste from basic active substances with a pronounced bitter taste, by precipitating insoluble salts from aqueous solutions of the active substances by means of polyanions, in particular neutralized copolymers of acrylic acid and/or methacrylic acid with lower alkyl esters of these acids, from CH 664,284, DE 27 52 705, and U.S. Pat. No. 4,539,199. The precipitated salts are then processed into tablets or suspensions. In this form, the insoluble salts are tasteless, but are, once again, converted into the original components after ingestion in the stomach, so that the active substance can be absorbed. In this way, preparations of chloroquines, ephedrine, doxepin, chlorpromazine, trimipramine, quinidine, benzyclan, papaverine, chloroanolol, and other active substances have been prepared. Hard-to-dissolve or insoluble salts of this type are prepared by reaction in a moistened powder mixture in accordance with EP 417,488. The processing of the insoluble salts to suspensions is not always satisfactory because of the danger of gradual demixing.

A method is also known from U.S. Pat. No. 3,629,392, in which a basic active substance is reacted with an aqueous dispersion of a polymer containing acid groups. The active substance is thereby bound to the surface of dispersed latex particles. In many cases, the dispersion coagulates by itself. Otherwise, coagulation agents are added in order to obtain a solid reaction product. The administration of an uncoagulated active substance-containing latex as a liquid preparation is not described.

SUMMARY OF THE INVENTION

One object of the invention is to provide a ranitidine preparation, in the form of an aqueous solution, which is completely free or substantially free of bitter taste. It was surprisingly discovered that, in contrast to numerous other basic active substances, the salts of ranitidine with polycarboxylic acids are water-soluble and after ingestion, are absorbable and thus fulfill the desired requirement.

For ranitidine hydrochloride, a bitter value of 100,000 is determined according to the well-known method described in the European Pharmacopoeia. On the other hand, the ranitidine preparations according to the invention exhibit bitter values below 1000, preferably below 750, which are considered easy to ingest.

The bitter taste of ranitidine hydrochloride can be attributed only to the taste effect of the ranitidine cation, since it is known that the chloride anion does not taste bitter, but rather salty. It was, therefore, surprising that the bitter taste can be suppressed by replacing the anion, whereas the ranitidine cation remains unchanged. While not being bound by any particular theory, it is suspected that the polyanion of the polycarboxylic acid cannot interact with the taste receptors because of its molecular size and that the ranitidine cations in the aqueous solution remain bound so strongly to the polyanion that they cannot reach the bitter taste receptors alone. When introduced into artificial gastric juice (0.1N HCl), free hydrogen ions can be detected almost completely after a few minutes.

By means of the invention, it is possible to prepare liquid, homogeneous ranitidine preparations for oral administration in the form of liquors or syrups. Furthermore, tablets or other solid medicinal forms which do not taste bitter even without encasing or encapsulation can be prepared from the dried salt.

DETAILED DESCRIPTION OF THE PREFERRED EMBODIMENTS

The salts of the invention can be prepared by reacting ranitidine hydrochloride or another water-soluble form of the active substance (ranitidine) or the free active substance base with a solution, suspension, or dispersion of a polycarboxylic acid. For complete salt formation, at least one equivalent quantity of carboxylic acid groups of the polycarboxylic acid is required per mole of ranitidine. Preferably, an excess of the polycarboxylic acid is used, for example, 2–5 carboxylic acid equivalents per mole of ranitidine. The reaction takes place very quickly in aqueous solution and the decline of the bitter taste can be monitored routinely.

As the polycarboxylic acid, one should consider those which are water soluble and physiologically compatible, at least in neutralized form, in the weakly alkaline range. Preferred are polycarboxylic acids with a molecular weight of at least 1,000 Daltons (D) and a carboxyl equivalent weight of 72–800, preferably 100–500 D. The molecular weights (as weight averages) generally lie, for example, between 10,000–200,000 D, preferably 50,000–150,000 D. With molecular weights below 1,000, the debittering effect declines. Polycarboxylic acids with a molecular weight above 200,000 produce very highly viscous solutions which are difficult to handle.

Preferred are alkali-soluble polymers or copolymers of acrylic acid and/or methacrylic acid, in particular consisting of 10–100, preferably 30–70 wt. % units of acrylic acid and/or methacrylic acid, and 90–0, preferably 70–30 wt. % units of one or more lower alkyl esters of the acrylic acid and/or methacrylic acid. Preferred are $C_{1-C4}$ alkyl esters, in particular methyl and ethyl esters. Noncrosslinked or, crosslinked, at least colloidally soluble polyacrylic acid and polymethacrylic acid can be obtained as commercial products. Suitable copolymers can be obtained as commercial products from Roehm GmbH, Darmstadt, under the trade names EUDRAGIT S or L and EUDISPERT hv, and are permitted for pharmaceutical preparations. Examples of such copolymers are the following:
poly(methylmethacrylate/methacrylic acid) 70:30, EUDRAGIT S100 poly(methylmethacrylate/methacrylic acid) 50:50, EUDRAGIT L100 poly(methylmethacrylate/methacrylic acid) 30:70, EUDISPERT hv poly (ethylacrylate/methacrylic acid) 50:50, EUDRAGIT L100-55 poly(ethylacrylate/methacrylic acid) 50:50, EUDRAGIT L30D If the polycarboxylic acid, in the form of a powder or an aqueous dispersion, is reacted with a ranitidine hydrochloride solution, a clear, colorless or at most a slight yellowish, homogeneous solution of ranitidine salts are obtained by stirring and heating to 40°–80° C., preferably 50°–90° C., and by adding a base. Foam formation, which sometimes appears, can be reduced by stirring under reduced pressure. The quantity of the base is preferably limited in such a way that a clear solution is just attained; as a rule, about 2 base equivalents per mole of ranitidine salt used are sufficient. Preferably, alkali metal hydroxides or carbonates are used as the base. If the free ranitidine base is processed, the alkali addition can generally be dispensed with. The pH value of the solution is generally about 4–8. The solids content of the solution can lie in the range of about 1–60, preferably 5–30 wt. %.

The solution can be used as such when ingested. Frequently, in order to improve acceptance, other additives are added—for example, sugars, such as sucrose or glucose, sweeteners, such as saccharin or sodium cyclamate, flavoring substances, aromas, dyes, stabilizers, thickeners and the like. As a commercial form, bottles are suitable, optionally with a dosing device, or ampules with individual dosages. The solution can also be dried gently, for example, by freeze-drying to form a solid product and can be ground to a powder. With the addition of the usual auxiliaries, tablets can be pressed therefrom, which can be taken without the bitter taste or optionally chewed or can be ingested after dissolving in water.

Having generally described this invention, a further understanding can be obtained by reference to certain specific examples which are provided herein for purposes of illustration only and are not intended to be limiting unless otherwise specified.

EXAMPLES

Example 1

Preparation of the solution 448 g Ranitidine HCl were dissolved in 1,100 g purified water and heated to 65° C. while stirring in a heatable boiler, which could be evacuated. Subsequently, 237 g EUDRAGIT L 100 were stirred in and stirring was continued for another 10 min. This was followed by the addition of a solution of 67.6 g sodium carbonate in 147.4 g water under reduced pressure. This suspension was stirred at 70° C. for 1 h.

The clear solution obtained was colorless to light yellowish and had a bitter value of approximately 500.

Example 2

5.0 g Ranitidine HCl, 4.4 g EUDRAGIT S 100 and 0.755 g sodium carbonate were reacted with 225 g purified water as described above. Subsequently, 260.0 g sucrose were dissolved in the clear liquid obtained. The final juice had a pleasant sweet and slightly bitter taste.

Example 3

5.0 g Ranitidine HCl were dissolved in 225 g purified water in a heatable boiler, which could be evacuated, and heated to 65° C. while stirring. Subsequently, 8.84 g EUDRAGIT L 30 D-55 were added and stirring was carried out for another 10 min. The addition of 0,755 sodium carbonate then took place under reduced pressure. This suspension was stirred at 70° C. for 1 h.

The clear solution obtained was colorless to light yellowish and had a only slightly bitter taste.

Example 4

5.0 g Ranitidine HCl, 1.99 g EUDISPERT hv, and 0.755 g sodium carbonate were reacted as in Example 2. Subsequently, 260.0 g sucrose were dissolved in the clear liquid obtained. The final juice had a pleasant sweet and slightly bitter taste.

Example 5

Preparation of a syrup 900 g of a solution prepared according to Example 1 were heated to 50° C., mixed with 900 g sucrose EP and stirred until a clear solution was obtained (approximately 10 min). The solution obtained, with a slightly increased viscosity, had a sweet, slightly bitter taste. The ranitidine content was approximately 10% by weight. The release of the ranitidine from the salt, photometrically measured in artificial intestinal juice (BP 88), occurred to 100% after 5 min.

Example 6

Preparation of chewing tablets

A solution prepared according to Example 1 was freeze-dried and the solid obtained was finely comminuted. 52.3 g sorbitol granules and a premixture (30 min) consisting of 20 g corn starch and 1 g sodium cyclamate were added to 267 g of this powder. The powders were placed in a double-cone mixer for 60 min and passed through a 1.5 mm mesh. Subsequently, 1 g magnesium stearate was added and mixed for 10 min. This powder was then pressed into tablets.

Obviously, numerous modifications and variations of the present invention are possible in light of the above teachings. It is, therefore, to be understood that within the scope of the appended claims, the invention may be practiced otherwise than as specifically described herein.

What is claimed as new and desired to be secured by Letters Patent of the United States is:

1. A ranitidine composition in the form of an aqueous solution, said aqueous solution comprising a polycarboxylic acid salt of ranitidine, wherein said polycarboxylic acid has a weight average molecular weight of 1,000 D–200,000 D.

2. The composition of claim 1, wherein said salt contains at least one equivalent of carboxyl groups of the polycarboxylic acid per mole of ranitidine.

3. The composition of claim 1, wherein said polycarboxylic acid has a weight average molecular weight of 10,000–200,000 D.

4. The composition of claim 3, wherein said molecular weight is 50,000–150,000 D.

5. The composition of claim 1, wherein said polycarboxylic acid has a carboxyl equivalent weight of 72–800 D.

6. The composition of claim 5, wherein said polycarboxylic acid has a carboxyl equivalent weight of 100–500 D.

7. The composition of claim 1, wherein said polycarboxylic acid is an alkali-soluble polymer or copolymer of acrylic acid, methacrylic acid or a combination thereof.

8. The composition of claim 7, wherein said polycarboxylic acid is a polymer or copolymer containing 10–100 wt. % monomer units of acrylic acid, methacrylic acid or a combination thereof and 90-0 wt. % monomer units of one or more lower alkyl esters of acrylic acid, methacrylic acid or a combination thereof.

9. The composition of claim 8, wherein said polycarboxylic acid is a copolymer of methylmethacrylate and methacrylic acid or a copolymer of ethylacrylate and methacrylic acid.

10. The composition of claim 1, having a bitter value below 1,000.

11. The composition of claim 10, having a bitter value below 750.

12. The composition of claim 1, having a solids content of about 1–60 wt. %.

13. A ranitidine composition in the form of an aqueous solution, said aqueous solution comprising a polycarboxylic acid salt of ranitidine, wherein said polycarboxylic acid has a weight average molecular weight of 1,000 D–200,000 D, said aqueous solution having a pH of about 4–8.

14. A ranitidine composition in the form of an aqueous solution, said aqueous solution comprising a polycarboxylic acid salt of ranitidine, wherein said polycarboxylic acid has a weight average molecular weight of 1,000 D–200,000 D, wherein said ranitidine composition is formed by mixing said polycarboxylic acid with an aqueous solution of free ranitidine base or with an aqueous solution of ranitidine hydrochloride and a base to form a mixture, and heating said mixture at a temperature of 40°–80° C. to form a solution having a pH of about 4–8.

* * * * *